US006004766A

United States Patent [19]
Atrache et al.

[11] Patent Number: 6,004,766
[45] Date of Patent: *Dec. 21, 1999

[54] METHOD FOR DETECTING LOW LEVELS OF MICROORGANISMS

[75] Inventors: Vincent H. Atrache, Lyons, France; Megan Ash, Mt. Colah; Ca Van Huynh, Granville, both of Australia

[73] Assignee: Biotechnology Australia Pty Limited, New South Wales, Australia

[ * ] Notice: This patent is subject to a terminal disclaimer.

[21] Appl. No.: 08/441,882

[22] Filed: May 16, 1995

Related U.S. Application Data

[62] Continuation-in-part of application No. 08/196,775, Feb. 14, 1994, Pat. No. 5,415,997, which is a continuation of application No. 08/002,549, Jan. 11, 1993, abandoned, which is a continuation of application No. 07/335,787, filed as application No. PCT/AU88/00274, Jul. 28, 1988, abandoned.

[30] Foreign Application Priority Data

Jul. 28, 1987 [AU] Australia .................................. PI3384

[51] Int. Cl.$^6$ ........................ G01N 33/53; G01N 33/543; G01N 33/537; G01N 33/569
[52] U.S. Cl. ........................ 435/7.94; 435/7.2; 435/7.32; 435/7.35; 435/7.3; 435/7.9; 435/29; 435/261; 435/34; 435/174; 436/518; 436/524
[58] Field of Search .................................... 435/7.2, 7.32, 435/7.35, 7.3, 7.92, 7.9, 7.94, 29, 34, 174, 261; 436/518, 524

[56] References Cited

U.S. PATENT DOCUMENTS

| | | |
|---|---|---|
| 3,970,518 | 7/1976 | Giaever et al. .............................. 435/5 |
| 4,525,452 | 6/1985 | Jones et al. . |
| 4,563,418 | 1/1986 | Ward, Jr. ...................................... 435/7 |
| 4,592,994 | 6/1986 | Mattiasson et al. . |
| 4,677,055 | 6/1987 | Dodin et al. ............................ 435/7.32 |
| 4,683,196 | 7/1987 | McLaughlin et al. .................. 435/7.32 |
| 5,369,011 | 11/1994 | Ebersole et al. . |
| 5,415,997 | 5/1995 | Atrache . |
| 5,486,452 | 1/1996 | Gordon et al. . |
| 5,491,068 | 2/1996 | Benjamin et al. . |

FOREIGN PATENT DOCUMENTS

| | | |
|---|---|---|
| WO 86/04352 | 7/1986 | Australia . |
| 2514367 | 4/1983 | France . |
| 8604352 | 7/1986 | WIPO . |

OTHER PUBLICATIONS

Voller et al. 1986. Manual Clinical Lab. Immunol. pp. 99–109.

Van Vuurde et al. 1985. In. Proceedings 6$^{th}$ Internatl Conf. on Plant Pathogenie Bacteria the Hague. pp. 835–842.

Mohit et al. "A Simple Single–Step Immunoimmobilisation Method for the Detection of Salmonella in the Presence of Large Numbers of Other Bacteria", *J Med Microbiol* 8:173–176 (1975).

Stannard et al. "Rapid Methods to Assess the Microbiological Quality of Foods," in Leatherhead Annual Report (1986).

La Roche et al. "Field Evaluation of the Membrane Filter–Disc Immunoibilization Technique in the Detection of Salmonellae in Egg Products," *Poultry Science* 60:2265–2269 (1981).

Macario et al., Monoclonal Antibodies against Bacteria, A.J.L. Ed. (1985) p. xxii.

Van Vuurde et al. "Principles and prospects of new serological techniquest including immunosorbent immunofluorescense, immunoaffinity isolation and immunosorbent enrichment for sensitive detection of phytopathogenic bacteria," In Proceedings of the 6th International Conference on Plant Pathogenic Bacteria, Beltsvelle, Nijofljunk. the Hague (1985).

Hranitzky et al. "Isolation of OI serovars of *Vibrio cholerae* from water by serologically specific method," *Science* 210:1025–1026 (1980).

Van Vuurde et al. "Immunosorbent immunofluorescense microscopy (ISIF) and Immunosorbent dilution plating (ISDP); new methods for detection of plan pathogenic bacteria," *Seed Science & 7 Technol.* II:523–533 (1983).

Tecra Technical Bulletin–Tecra Salmonella Immnocapture System.

Faber et al. "Monoclonal Antibodies Directed Against the Glagellar Antigens of Listeria Species and Their Potential in EIA–Based Methods," *J. of Food Protection* 50:(6) 479–484 (Jun. 1987).

Seeliger et al. "Serotyping of Listeria Monocytogenes and Related Species," *Methods in Microbiology* 13:31–49(1979).

Paterson et al. "Flagellar Antigens of Organisms of the Genus Listerella," *Institute of Animal Pathology*, University of Cambridge, pp. 25–32.

Marfleet, et al. "Listeria Monocytogenes as a Food–Borne Pathogen," *Scientific and Technical Surveys* No. 157 (Feb. 1987).

(List continued on next page.)

*Primary Examiner*—Nita Minnifield
*Attorney, Agent, or Firm*—Foley & Lardner

[57] ABSTRACT

A method is provided for the detection of low levels of a microorganism in a sample in the presence of competing microflora, comprising the steps of: (a) exposing the sample to a solid support to which are adsorbed antibodies specific for said microorganism; (b) washing the solid support to remove unbound material; (c) combining the solid support with sterile nutrient broth which permits replication of said microorganism; (d) incubating the solid support with said nutrient broth at a temperature and for a time sufficient to allow said microorganism to replicate and be recaptured by said antibodies on said solid support; (e) releasing the bound microorganism from the solid support into a solution; and (f)assaying the solution for the microorganism. A kit for performing the assay also is provided. This kit comprises a solid support to which are adsorbed antibodies specific for the microorganism, a first container comprising a washing solution, a second container comprising a sterile nutrient broth, and, optionally, a third container comprising a solution comprising a releasing agent.

33 Claims, No Drawings

OTHER PUBLICATIONS

Lovett, J. "Listeria Isolation," *In Bacteriological Analytical Manual*, 6th edition, (1984) Chapter 29.

Van Vuurde et al. "New Approach in Detecting Phytopathogenic Bacteria by Combined Immunoidentification Assays," *Bulletin OEPP/EEPO Bulletin* 17:139–148 (Nov. 1987).

Clark, et al. "Enzyme–Linked Immunosorbent Assay (ELISA): Theoretical And Practical Aspects," *in Enzyme Immunoassay*, (E.T. Maggio. ed.) 167–79 (1980).

Van Vuurde, et al. "Detecting Seedborne Bacteria by Immunofluorescence," In Proceedings of the 6th International Conference on Plant Pathogenic Bacteria, Beltsvelle. Nijhofjunki. the Hague (1987).

METHOD FOR DETECTING LOW LEVELS OF MICROORGANISMS

This application is a continuation-in-part of U.S. Ser. No. 08/196,775, filed Feb. 14, 1994, now U.S. Pat. No. 5,415, 997, which is a continuation of U.S. Ser. No. 08/002,549, filed Jan. 11, 1993, now abandoned, which is a continuation of Ser. No. 07/335,787, filed May 26, 1989, now abandoned which is 371 of PCT/AU88/00274 filed Jul. 28, 1988.

TECHNICAL FIELD

The current invention relates to methods for detecting low levels of a particular microorganism, or microorganisms from a mixed culture or sample using antibodies and solid immunosorbent supports without the need for a preliminary or further growth step in selective media.

BACKGROUND ART

Solid-phase immunoassays, based either on enzymes or radioactive isotopes as labels have found wide application in diagnostic microbiology due to their high specificity and sensitivity.

The specificity of an immunoassay is determined by the antibody or antigen which has been immobilized on the solid support. A major advantage of a solid phase assay is that on completion of the immune reaction, unwanted material is easily and rapidly separated from the antigen-antibody immune complex by a simple washing step. A wide variety of solid supports have found application for antibody or antigen immobilization and include polystyrene, polyvinyl chloride, nylon, titanous hydroxide, agarose beads and nitrocellulose.

The successful application of immunoassays to the detection of microorganisms in a sample is possible only if the particular organism of interest is present in sufficient numbers. This critical concentration is determined by the sensitivity of the immunoassay which can vary greatly depending on the affinity and avidity of a particular antibody for its antigen. It is for this reason that many immunoassays require culturing of the sample prior to performing the test.

This usually involves a pre-enrichment step to resuscitate injured microorganisms followed by a selective enrichment to increase the numbers of the microorganism of interest. Selecting culture conditions which favour the growth of a particular microorganism over its competitors has traditionally involved the use of either antibiotics, specific nutritional requirements or manipulation of the physical characteristics of the growth medium, e.g. temperature. These methods can take one to two days or several weeks depending on the organism and the extent of contamination with other microflora.

The use of immunosorbents for selecting microorganims from a mixed population is known. The sorbent immobilizes a predetermined species of microorganism against which the antibodies are directed. Cells captured in this way can be incubated in a growth medium and then counted by such traditional techniques as plating and colony counting.

U.S. Pat. No. 4,592,994 describes a method for the determination or identification of microorganisms or unicellular organisms in a sample. The method involves exposing the sample to an absorbent having "a specific binding power" which may be provided by an antibody raised against the microorganism to be detected. Unbound sample is separated and the adsorbent with bound organisms is exposed to a nutrient medium to initiate metabolism. This nutrient medium undergoes physical or chemical changes as a result of this metabolism and these changes are observed in conjunction with calibration curves to determine presence and amount of the relevant microorganism. The assay involves indirect detection of original numbers of organisms through detection of metabolites in the medium. This may generate problems with regard to the specificity of the assay since different microorganisms may share metabolites.

U.S. Pat. No. 4,563,418 describes a method for the detection of a particular motile organism in a sample, for example, flagellate bacteria such as Salmonella species.

The method involves enriching the sample in an enrichment medium selective for the particular motile organism and filling a motility vessel with a non-selective medium containing a chemotactic attractant which serves to temporarily immobilize the organism of interest and its competitors in the medium for some time after inoculation. Antibodies specific to the flagella of the particular motile microorganism are added through another opening in the motility vessel. The vessel is incubated under sufficient temperature and time conditions to permit the motile organisms to metabolize the chemotactic attractant, thereby reducing its concentration sufficiently to allow movement of the organisms present with the result that the organisms move through the medium and the particular motile organisms being assayed are immobilized by the antibodies. The quantity of antibody used is sufficient to produce a permanent immobilization band.

In Mohit et al ["A Simple Single-step Immunoimmobilization Method for the Detection of Salmonella in the Presence of Large Numbers of Other Bacteria" J. Med. Microbiol. 8 173 (1975)], a method of detecting Salmonella in a mixed population is described. This method employs a selective semi-solid medium, which promotes the migration of Salmonella, followed by immobilization using polyvant H antisera.

La Roche et al in "Field Evaluation of the Membrane Filter-Disc Immobilization Technique in the Detection of Salmonella in Egg Products" describes a method for detecting Salmonella which involves using a membrane filter to concentrate Salmonella from a primary enrichment broth before selective migration in order to increase recovery.

Stannard reported in the annual report for Leatherhead RA for 1986, investigations into separation of Salmonella from other organisms, with a view to reducing the time required for detection of Salmonella in samples.

This method relied on antibody-coated magnetic particles. However, it was found that the apparent enrichment of Salmonella over other closely related organisms was in fact due to differential affinity of these organisms to the glassware used in the experiment. Attempts to use this differential affinity for glass to enrich Salmonella were unsuccessful due to the lack of specificity of the effect.

Thus it can be seen that the prior art methods for detecting microorganisms from mixed populations provide means for detecting low numbers where enrichment in selective medium is used. Immunoimmobilization has been used but has not been shown to be effective for detecting low numbers in the absence of a such a selection on selective medium.

The current invention provides methods for detecting low numbers of a particular microrganism or microorganisms in a mixed population which overcome the need for pre-selection in selective media by using an immunoimmobilization technique followed by non-selective growth and immunoassay or by cleavage of the antibody-microorganism bond and growth of the microorganisms on non-selective media.

The methods can be especially usefully applied to detecting Salmonella and Listeria spp meeting the need for rapid, sensitive methods for their detection in mixed populations.

DESCRIPTION OF THE INVENTION

The invention provides methods for the rapid detection of a particular microorganism, or microorganisms, in the presence of competing micro-flora using specific antibodies adsorbed onto a solid support. The immobilized antibody is to an antigen of the microorganism which allows selective capture and immobilization of the desired microorganism without compromising its ability to replicate. Appropriate antibodies can be raised against surface antigens provided by such surface structures as flagella or lipopolysaccharides. Selective concentration of the desired microorganism or microorganisms onto the solid support allows rapid separation from competing microflora in the sample and is achieved by simply washing the solid support. The immobilized cells can then be transferred to a nutrient broth to allow replication during which time the multiplying microorganisms will continue to be captured and immobilized on the solid support until the antibody sites are saturated.

The time taken for the concentration of the microorganisms to reach a detectable level will depend on the generation time of the particular microorganism or microorganisms and on the sensitivity limits of the immunoassay.

Once a detectable level is reached the solid support is simply separated from the culture broth, then washed and assayed directly.

Alternatively, the antibody-microorganism bond can be broken by an appropriate releasing agent, heat or mechanical means, resulting in the release of the microorganism. The released cells can be transferred to a nutrient medium to allow replication and detection of colonies that form.

The selection of the microorganism or microorganisms during the immunoimmobilization step can involve selection of surface antigens that are common to a genus, to a particular species within that genus or if very high selectivity is required, antigens that are specific to a serotype of that species may be chosen.

This technique thus eliminates the need for elaborate and expensive enrichment media in providing rapid sensitive detection of low levels of a particular microorganism or microorganisms from mixed populations.

In a first embodiment, the invention provides a method for detecting low levels of a particular microorganism or microorganisms in the presence of competing microflora in a sample which method comprises: exposing the sample to a solid support to which are adsorbed antibodies specific for the microorganism or microorganisms being detected, said antibodies being capable of selective capture and immobilisation of the microorganism or microorganisms without compromising the ability of the microorganism or microorganisms to replicate; washing the support to remove unbound materials; adding sterile nutrient broth to the support; incubating the support in the nutrient broth at a temperature and for a time relative to the generation time of the microorganism or microorganisms sufficient to allow the microorganism or microorganisms to reach a detectable level; washing the support and then performing an immunoassay on the support using an immunoreagent specific for the microorganism or microorganisms being detected.

Preferably the antibody is raised against a surface antigen of the microorganism. More preferably the surface antigen is a flagellar protein or lipopolysaccharide.

In a preferred form, the antibodies are immobilized onto a solid support comprising a bead, tube or well.

Preferably, the support material is polystyrene, polyvinyl chloride, nylon, titanous hydroxide, agarose beads or nitrocellulose.

Preferred microorganisms according to the invention include Salmonella species, Listeria species and *E. coli* species.

The exposure of the sample to the antibody-coated support is generally for 1 hour or less, typically for about 20 to about 60 minutes. The wash steps are preferably performed using sterile saline buffer, more preferably Tris-saline buffer, or sterile buffered peptone water solution. Virtually any nutrient broth may be used in the method, however, preferred broths are tryptone soya broth, M broth and tryptone soya broth/yeast extract nutrient broth. The incubation in nutrient medium may be overnight and is usually at 37° C. For example, Salmonella samples may be incubated at 37° C. for 4–6 hours, some Salmonella samples, such as chicken samples, may be incubated at 42° C. for 4–6 hours, for example for 5 hours, and Listeria samples may be incubated at 28–30° C. for about 6 hours. For detection of *Salmonella typhimurium*, incubation times of approximately 4–6 hours have been shown to be effective. Where higher numbers of the particular microorganism are present in the original sample incubation times of between 1 and 6 hours can be used. Preferably, the immunoassay is an ELISA.

In a more preferred form the method comprises: exposing a Salmonella test sample for between about 5 and about 30 minutes to a polystyrene support to which are adsorbed anti-Salmonella flagella antibodies, said antibodies being capable of selective capture and immobilisation of Salmonella without compromising the ability of the Salmonella to replicate; washing the support to remove unbound material; adding sterile nutrient broth to the support; incubating the support at 37° C. for between about 1 and about 6 hours; washing the support; adding an enzyme-labelled antibody specific to Salmonella; incubating for between about 5 and about 30 minutes; discarding any excess enzyme-labelled antibody; washing the support; adding a chromogenic substrate specific for the enzyme of the enzyme-labelled antibody; and measuring conversion of the chromogenic substrate to a coloured compound.

Preferably the support is a tube, bead, microtitre well or dipstick.

Preferably the enzyme-labelled antibody is an (anti-Salmonella) antibody—peroxidase conjugate. However, it is recognised that it is possible to use an unlabelled anti-Salmonella antibody in conjunction with a labelled antibody raised against the anti-Salmonella antibody in an indirect version of the assay for bound Salmonella.

Preferably the wash is performed using a Tris-saline solution as wash solution.

Preferably the substrate is an $ABTS/H_2O_2$ solution.

Preferably the nutrient broth is tryptone soya broth.

In a second embodiment the invention provides a method for detecting low levels of a particular microorganism or microorganisms in the presence of competing microflora in a sample which method comprises: exposing the sample to a solid support to which are adsorbed antibodies specific for the microorganism or microrganisms, said antibodies being capable of selective capture and immobilisation of the microorganism or microorganisms without compromising the ability of the microorganism or microorganisms to replicate; washing the support to remove unbound material; releasing the bound microorganism or microorganisms with a releasing agent by heating the support, or by mechanical means; adding the released material to a nutrient medium; and incubating at a temperature and for a time relative to the generation time of the microorganism or microorganisms being detected to allow the microorganism or microorganisms to reach a detectable level.

Releasing agents suitable for dissociating the antibody-microorganism bond include:

1) chaotropic agents such as 4.5 M $MgCl_2$ pH 7.5 or 2.5M NaI pH 7.5
2) polarity reducing agents such as ethylene glycol in solutions of up to 50%
3) pH change inducing agents such as glycine/HCl pH 2.5, aqueous $NH_3$ pH 11 or 0.5% KOH pH 12.5.

The microorganisms also may be released by heating the support to release the bound microorganisms into a solution, or by mechanical means, such as by vigorously shaking, sonicating or vortexing the support to release the bound microorganisms into a solution.

Preferably the releasing agent is 0.5% KOH pH 12.5. To this solution protein may be addded to provide a carrier for the released microorganisms.

In a preferred form the microorganisms are Listeria species or Salmonella species, more preferably *Listeria monocytogenes*.

It is recognised that prior to the release of the bound microorganisms they may also be subjected to a non-selective growth in nutrient medium to increase their numbers prior to release and detection.

The sample is preferably exposed to the antibody coated support for approximately 5 minutes. The wash solution is preferably a sterile saline solution, more preferably sterile Tris-HCl buffered saline pH 7.5. Virtually any nutrient medium may be used, however, Trypticase soya agar is a preferred medium. The plates are preferably incubated at 37° for between 18 and 24 hours. By using nutient medium in place of selective media incubation can be reduced to as short a time as 12 hours.

In a more preferred form the method comprises: exposing a Listeria test sample for about 5 minutes to a polystyrene support to which are adsorbed antibodies specific to Listeria species, said antibodies being capable of selective capture and immobilisation of Listeria species without compromising the ability of the Listeria species to replicate; washing the support to remove unbound material; releasing the bound Listeria with a releasing agent; adding the released material to a nutrient agar plate; and incubating the plate for about 16–18 hours at 37° C.

Preferably the antibodies are (anti-Listeria flagella) antibodies.

Preferably the releasing agent is a 0.5% KOH solution.

Preferably washing is performed using a Tris/Saline pH 7.5 solution.

Preferably the nutrient agar plate is a trypticase soya agar plate.

The invention also provides a test kit for the detection of low levels of a particular microorganism or microorganisms in a mixed population which kit comprises: a solid support to which are adsorbed antibodies specific for the microorganism or microrganisms being detected; a wash solution; an enzyme-labelled antibody specific for the microorganism or microorganisms being detected; and a solution of a chromogenic substrate for the enzyme of the enzyme-labelled antibody.

In place of the enzyme-labelled antibody the kit may comprise an anti-microorganism antibody together with an enzyme-labelled antibody raised against the anti-microorganism antibody.

The invention also provides a test kit comprising: a solid support to which are adsorbed antibodies specific for the microorganism or microorganisms being detected; a releasing agent; and a wash solution.

The invention also provides a kit comprising a solid support to which are adsorbed antibodies specific for the microorganism or microorganisms being detected, and, in suitable containers, a washing solution and a nutrient medium. In a preferred embodiment, the solid support and containers are adapted such that the solid support may be inserted into the containers. This kit also may comprise a third container comprising a solution comprising a releasing agent.

The invention is further described with reference to the following examples which are in no way limiting on the scope of the invention.

EXAMPLE 1

Selective Isolation of Salmonella using Antibody Coated Wells

*Salmonella typhimurium* (inhouse strain BTA 438) and *Citrobacter diversus* (BTA 1323) were inoculated into individual M broth solutions and were incubated overnight at 37° C. Each of the cultures grew to $10^9$ organisms/ml. These were then diluted as follows:

$10^8$ cells/ml *C. diversus* with $10^4$ cells/ml *S. typhimurium*
$10^8$ cells/ml *C. diversus* with $10^3$ cells/ml *S. typhimurium*
$10^8$ cells/ml *C. diversus* with $10^2$ cells/ml *S. typhimurium*
$10^8$ cells/ml *C. diversus* with $10^1$ cells/ml *S. typhimurium*
$10^8$ cells/ml *C. diversus* with $10^0$ cells/ml *S. typhimurium*
$10^8$ cells/ml *C. diversus* only (control)

Polystyrene wells coated with highly purified antibodies to Salmonella flagella were then added to the M broths containing the mixed cultures. Wells coated with non-immune sheep immunoglobulin were placed into a duplicate set of mixed cultures as a control. The broths containing the wells were shaken for 1 hour at 37° C.

The wells were then carefully removed and washed 3 times in Tris-saline, then placed in fresh M broth solutions. These M broths were incubated overnight at 37° C. to allow the immobilised organisms to multiply. The wells were then removed from the M broths and an ELISA was performed on them.

EIA Method

The wells were washed three times with Tris-saline-Tween™ (TST), then anti-Salmonella IgG—Horseradish Peroxidase labelled conjugate was added. After 30 minutes incubation at 37° C., the wells were washed three times with TST, then substrate (2,2-azinobis(3-ethylbenzthiazoline sulfonic acid)) in citrate-phosphate buffer (0.1M, pH 4) containing hydrogen peroxide (0.005%) was added and colour allowed to develop.

| ORGANISMS/ML | | | OPTICAL DENSITY[1] | |
|---|---|---|---|---|
| | | | Salmonella Ab | Control |
| *C. diversus* | | *S. typhimurium* | Coated Wells | Wells[2] |
| $10^8$ | + | $10^4$ | 2.0 | 0.026 |
| $10^8$ | + | $10^3$ | 1.378 | 0.035 |
| $10^8$ | + | $10^2$ | 0.306 | 0.063 |
| $10^8$ | + | $10^1$ | 0.314 | 0.042 |
| $10^8$ | + | $10^0$ | 0.066 | 0.050 |
| $10^8$ | | | 0.078 | 0.037 |

[1]Optical densities read using dual wavelength ELISA reader at 414 nm and 490 nm.
[2]Non-immune sheep immunoglobulin coated wells.

EXAMPLE 2

The method was compared with the Standard Culture Enrichment protocol [AOAC Official Methods of Analysis 963–971 (1984)] and showed increased speed of performance, and enhanced selectivity and sensitivity as described below.

The protocol was as described in Example 1 except that 1 ml of the M broth containing the mixed cultures was placed into 10 ml of tetrathionate broth and incubated at 37° C. for 6 hours.

Following this, an ELISA was performed on the broths. To the remaining 9 ml of broth, wells coated with highly purified antibodies to Salmonella flagella were added and the procedure of Example 1 followed except that the incubation of the M broth was for 6 hours only and then an ELISA was performed.

Results

|  | Colonies Counted | | | |
| --- | --- | --- | --- | --- |
|  | Immuno-enrichment | | Direct Plating | |
| Sample Tested | Listeria | Other | Listeria | Other |
| Mixture A | 253 | 222 | 0 | >1000 |
| Mixture B | 125 | 264 | 0 | >1000 |
| S. aureus $10^9$ cells/ml | — | 246 | — | >1000 |
| S. faecalis $10^9$ cells/ml | — | 500 | — | >1000 |
| L. monocytogenes $10^6$ cells/ml | 127 | — | >1000 | — |

In a single step, approximately a one thousand fold enrichment of L. monocytogenes over the competing microorganism was achieved. Isolation was greatly simplified and

| ORGANISMS/ML | | OPTICAL DENSITY[1] | |
| --- | --- | --- | --- |
| | | SALMONELLA Ab | TETRATHIONATE |
| C. DIVERSUS | S. TYPHIMURIUM | COATED WELLS | BROTHS |
| $10^8$ | + $10^4$ | 2.0 | 0.113 |
| $10^8$ | + $10^3$ | 2.0 | 0.089 |
| $10^8$ | + $10^2$ | 0.244 | 0.076 |
| $10^8$ | + $10^1$ | 0.200 | 0.061 |
| $10^8$ | control | 0.030 | 0.065 |

[1]Optical densities read using dual wavelength ELISA reader at 414 nm and 490 nm.

After 6 hours the ELISA detected $10^3$ Salmonella in the presence of $10^8$ Citrobacter from the coated wells whilst after 6 hours selective enrichment in tetrathionate no Salmonella were detected by the ELISA.

EXAMPLE 3

Selective Isolation of Listeria monocytogenes from Mixed Cultures

Listeria monocytogenes (BTA No. 1767), Staphylococcus aureus (BTA No. 1414), and Streptococcus faecalis (ATCC No. 19433) were individually cultured in Tryptose-Soya broth overnight at 28° C. Each of the cultures grew to a minimum of $10^9$ organisms/ml and were then diluted and mixed as follows:

Mixture A: $10^9$ cells/ml Staphylococcus aureus+$10^6$ cells/ml L. monocytogenes.

Mixture B: $10^9$ cells/ml Streptococcus faecalis+$10^6$ cells/ml L. monocytogenes.

Controls: $10^9$ cells/ml S. faecalis $10^9$ cells/ml S. aureus $10^6$ cells/ml L. monocytogenes A 200 µl sample from each of the above cultures was incubated in a polystyrene well, precoated with highly purified antibodies to Listeria flagella. After 5 minutes incubation at room temperature the wells were emptied and washed three times with sterile Tris-HCl buffered saline pH 7.5. Any captured organisms were then released into solution by the addition of 0.5% KOH solution pH 12.5 (100 µl) and immediately transferred to Tryptose Soya Agar plates and spread using a glass spreader. For comparative purposes each of the cultures above was also examined directly without immunoenrichment by streaking a 10 µl aliquot onto Tryptose Soya Agar. All plates were incubated for 18–24 hours at 37° C. and then examined under oblique light for typical colonies of Listeria monocytogenes (sparkling blueish-grey, transluscent, 0.5–1.5 mm in diameter, watery consistency).

detection was possible when direct plating of such a mixture failed to isolate a Listeria colony.

EXAMPLE 4

Sensitivity of Immunoenrichment for the Isolation of Listeria monocytogenes

Listeria monocytogenes was cultured in Tryptose Soya Broth for 18 hours at 28° C. The culture was then diluted in sterile saline to give concentrations of $10^7$, $10^6$, $10^5$ and $10^4$ organisms/ml. Samples (200 µl) of each dilution, tested in triplicate, were incubated in individual anti-Listeria antibody coated wells for 5 minutes then the wells emptied and washed with sterile buffered saline pH 7.5. Any immobilized microorganisms were released into solution by the addition of 0.5% KOH solution pH 12.5 and then immediately transferred to Tryptose Soya Agar plates and spread using a glass spreader. Plates were incubated at 37° C. for 18–24 hours and the number of colonies counted.

| Number of organisms added/well | No. of Colonies counted |
| --- | --- |
| $2 \times 10^6$ | 1000 |
| $2 \times 10^5$ | 300 |
| $2 \times 10^4$ | 50 |
| $2 \times 10^3$ | 1 |

Sensitivity of the method allowed detection of Listeria monocytogenes when as few as $2 \times 10^3$ organisms were incubated in the antibody coated well.

EXAMPLE 5

General Method:

A Listeria test sample was adjusted to pH 7.5–8.0 and 200 µl were transferred into a USA Dynatech Removawell™ which has been coated with anti-Listeria antibodies in 10 mm phosphate buffer pH 8.1, 10 µg/ml O/N at 20–25° C.

The sample was incubated at room temperature for 5 minutes.

The well was then washed gently with sterile Tris-Saline solution at pH 7.5.

100 μl of KOH (pH 11.1) was added.

A 100 μl aliquot of the resulting KOH mix was transferred to a Tryptone soya agar or modified McBride agar plate and spread using a glass spreader. The plate was incubated for between 18 and 24 hours at 37° C. and the plate examined for typical Listeria colonies.

Optimization of Reaction of Reaction Time for Immunoenrichment

Culture: Listeria monocytogenes (BTA 1767) was grown in OXOID's™ TSB+0.6% yeast extract at 28° C. overnight.
Releasing reagent: 0.5% KOH (pH 10.5).
Plate: Modified McBride Agar plate.

| Microorganisms | No. of Listeria colonies isolated on MMA plate | | | | |
|---|---|---|---|---|---|
| | 5 min. | 10 min. | 15 min. | 20 min | 30 min. |
| * $10^5$ cells/ml of L.m. | 58 | 54 | 37 | 7 | 15 |
| * $10^5$ cells/ml of L.m.+ $10^9$ cell/ml Streptococcus faecalis | 100 | 100 | 84 | — | 10 |

Immuno-enrichment for Listeria using different releasing reagents.

| Listeria monocytogenes dilution | Releasing reagent | No. of colonies on TSA plate |
|---|---|---|
| ($2 \times 10^6$ cell/ml) | 0.01% KOH + 0.85% NaCl | 145 |
| " | " | 149 |
| ($2 \times 10^6$ cell/ml) | 0.01% NaOH + 0.85% NaCl | 191 |
| " | " | 260 |
| ($10^6$ cell/ml) | 0.01% KOH + 0.85% NaCl | 122 |
| " | 0.01% NaOH + 0.85% NaCl | 145 |
| " | " | 118 |
| " | 10 mM Tris (pH 11.1) + 0.85% NaCl | 112 |
| " | 10 mM Tris (pH 11.1) + 0.85% NaCl | 161 |

| Listeria innocua (CT-94) | Releasing reagent | No. of colonies on TSA plates |
|---|---|---|
| " | 0.01% KOH + 0.85% NaCl | 58 |
| " | " | 65 |
| ($10^6$ cell/ml) | 0.1M $Na_2CO_3$ (pH 11.1) | 163 |
| " | " | 126 |

Specificity of Immunoenrichment (1) Culture: All cultures were grown in OXOID's™ TSB at 28° C. overnight.
Releasing reagent: 0.01% KOH+0.85% NaCl (pH 11.1)
Microtitre wells: Listeria antibody coated wells.
Staphylococcus exterotoxin antibody coated well.
Blank well (normal gamma irradiated polystyrene well).

| Mixture of microorganisms | Type of well | No. of Listeria on TSA plate |
|---|---|---|
| * $10^8$ cell/ml L. monocytogenes + $10^8$ cell/ml of Rhodococcus equi + $10^9$ cell/ml Staphylococcus | Listeria antibody coated well | 2,000–3,000 |
| * The same mixture as above | | 2,000–3,000 |
| | Staphylococcus exterotoxin antibody coated well. | 0 |
| | | 0 |
| * The same mixture as above | Blank well | 0 |
| | | 1 |

EXAMPLE 6

Salmonella Rapid Detection Kit

This kit enables the user to rapidly test for the presence of Salmonella in food, environmental or clinical samples. Highly specific antibodies to Salmonella flagella coated onto the surface of polystyrene tubes are used to capture Salmonella organisms present in a test sample. This is achieved by incubating the test sample in the antibody coated tube for a short time e.g: 5–30 minutes. The tube is then washed thoroughly to remove unbound material. Sterile nutrient broth e.g: Tryptone soya broth is then added and the tube incubated at 37° C. for 1–6 h. During this time the immobilised Salmonella replicate and continue to be captured by available antibodies on the tube surface. This allows for a sufficient concentration of organisms to be reached for subsequent detection by immunoassay.

The presence of the captured organisms can now be detected by discarding the culture broth and then adding an enzyme-labelled antibody specific to Salmonella. After a short incubation (5–30 min) excess enzyme-antibody reagent is discarded and the tube washed.

The enzyme-antibody conjugate which has specifically bound to the immobilised organisms is detected by addition of a substrate for the enzyme.

Materials Provided
  anti-Salmonella antibody coated polystyrene tubes
  anti-Salmonella-antibody-Peroxidase conjugate
  wash solution Tris Saline Tween™
  Substrate solution—ABTS/$H_2O_2$ By use of Listeria reagents in the place of the Salmonella reagents this kit can be adapted to the detection of Listeria.

Listeria Detection Kit

The kit allows the selective isolation of Listeria from culture broths derived from either food or environmental samples and eliminates the need to develop/use selective agar plates for the isolation of the organism.

Highly specific antibodies to Listeria are immobilised on the internal surface of polystyrene tubes provided. An aliquot of the test solution is incubated in the antibody coated tube for a specified time (5 minutes). The tube is then emptied and washed to remove unbound material. Any captured Listeria is then released by the addition of a releasing agent e.g. 0.5% KOH solution. The Listeria released into solution are spread onto a nutrient agar e.g. Trypticase soya agar and the plate incubated for 16–18 hours at 37° C. to allow the organisms to replicate.

By this procedure the desired organism is readily isolated from an initial culture broth, (sample) contaminated with a variety of other organisms and thus obviates the need for selective agars. In the specific case of Listeria the described method shows superior selectively over the selective agars currently recommended by the Microbiological Standard Methods.

Materials Provided
(1) Anti-Listeria flagella antibody coated polystyrene tubes
(2) Releasing agent (0.5% KOH solution)
(3) Wash Buffer Tris/Saline pH 7.5

By replacing the Listeria reagents with Salmonella reagents this kit can be adapted to the detection of Salmonella.

These examples illustrate the usefulness of these methods for the rapid detection of a specific organism in a mixed culture.

The methods are more rapid than traditional culture enrichment protocols, with a positive result being obtainable as rapidly as 6 hours, compared to a minimum of 48 hours by standard culture methods.

Industrial Application

The current invention provides an alternative to use of specialized selection media for the detection of low numbers of a particular microorganism or microorganisms in a mixed population.

We claim:

1. A method for the detection in a sample, in the presence of competing microflora, of low levels of a particular microorganism selected from the group consisting of a genus, a species and a serotype, comprising the steps of:
    (a) exposing said sample to a solid support to which are adsorbed antibodies specific for said microorganism;
    (b) washing said solid support to remove unbound material;
    (c) combining said solid support with sterile nutrient broth which permits replication of said microorganism;
    (d) incubating said solid support with said nutrient broth at a temperature and for a time sufficient to allow said microorganism to replicate and be recaptured by said antibodies on said solid support, whereby a detectable level of said microorganism on said solid support is reached;
    (e) releasing said bound microorganism from said solid support into a solution; and
    (f) assaying said solution for said microorganism, thereby detecting said microorganism.

2. The method according to claim 1, wherein said antibodies are specific for a surface antigen of said microorganism.

3. The method according to claim 2, wherein said surface antigen is a flagellar protein or lipopolysaccharide.

4. The method according to claim 1, wherein said solid support is selected from the group consisting of a bead, a tube and a well.

5. The method according to claim 1, wherein said solid support is a dipstick.

6. The method according to claim 1, wherein said solid support is made of a material selected from the group consisting of polystyrene, polyvinyl chloride, nylon, titanous hydroxide, agarose and nitrocellulose.

7. The method according to claim 1, wherein said microorganism is selected from the group consisting of Salmonella species and Listeria species.

8. The method according to claim 1, wherein said microorganism is an *E. coli* species.

9. The method according to claim 1, wherein said sample is exposed to said solid support for no more than one hour.

10. The method according to claim 9, wherein said sample is exposed to said solid support for about 20 to about 60 minutes.

11. The method according to claim 1, wherein, in step (b), said solid support is washed with a sterile buffered saline solution.

12. The method according to claim 1, wherein, in step (b), said solid support is washed with a sterile buffered peptone water solution.

13. The method according to claim 1, wherein said nutrient broth is selected from the group consisting of tryptone soya broth and M broth.

14. The method according to claim 1, wherein said nutrient broth is tryptone soya broth/yeast extract nutrient broth.

15. The method according to claim 1, wherein, in step (d), said solid support is incubated in nutrient broth at 37° C. for about 6 hours.

16. The method according to claim 1, wherein, in step (d), said solid support is incubated in nutrient broth at 37° C. for between about 12 to about 24 hours.

17. The method according to claim 1, wherein said microorganism is a Salmonella species, and wherein, in step (d), said solid support is incubated in nutrient broth at 37° C. for about 4 hours.

18. The method according to claim 1, wherein said microorganism is a Salmonella species, and wherein, in step (d), said solid support is incubated in nutrient broth at 42° C. for about 5 hours.

19. The method according to claim 1, wherein said microorganism is a Listeria species, and wherein, in step (d), said solid support is incubated in nutrient broth at 28–30° C. for about 6 hours.

20. The method according to claim 1, wherein said step (e) of releasing said bound microorganism comprises contacting said support with a solution comprising a releasing agent.

21. The method according to claim 20, wherein said releasing agent is selected from the group consisting of a chaotropic agent, a polarity reducing agent, and a pH change inducing agent.

22. The method according to claim 21, wherein said solution comprising a releasing agent is selected from the group consisting of a 4.5 M $MgCl_2$ solution with a pH of 7.5, a 2.5 M NaI solution with a pH of 7.5, ethylene glycol solutions with a concentration of up to 50%, a glycine/HCl solution with a pH of 2.5, an aqueous $NH_3$ solution with a pH of 11 and a 0.5% KOH solution with a pH of 12.5.

23. The method according to claim 20, wherein said solution comprising a releasing agent further comprises a protein.

24. The method according to claim 22, wherein said solution comprising a releasing agent is a 0.5% KOH solution with a pH of 12.5.

25. The method according to claim 1, wherein said step (e) of releasing said bound microorganism comprises exposing said support to heat.

26. The method according to claim 25, wherein said step (f) of assaying said solution for said microorganism comprises performing an immunoassay on said solution using an immunoreagent specific for said microorganism.

27. The method according to claim 1, wherein said step (e) of releasing said bound microorganism comprises the use of mechanical means to release said bound microorganism from said solid support.

28. The method according to claim 27, wherein said mechanical means is selected from the group consisting of shaking, sonicating and vortexing said solid support.

29. The method according to claim 1, wherein said step (f) of assaying said solution for said microorganism comprises performing an immunoassay on said solution using an immunoreagent specific for said microorganism.

30. The method according claim 29, wherein said immunoassay is an ELISA.

31. The method according to claim 30, wherein said immunoreagent is an enzyme-labeled, anti-microorganism antibody.

32. The method according to claim 30, wherein said immunoreagent comprises an anti-microorganism antibody and an enzyme-labeled antibody specific for said anti-microorganism antibody.

33. The method according to claim 1, wherein said step (f) of assaying said solution for said microorganism comprises plating said microorganisms onto agar plates, incubating said plates, and examining said plates for colonies of said microorganism.

* * * * *

UNITED STATES PATENT AND TRADEMARK OFFICE
CERTIFICATE OF CORRECTION

PATENT NO. : 6,004,766 Page 1 of 1
DATED : December 21, 1999
INVENTOR(S) : Vincent H. Atrache, Megan Ash and Ce Van Huynh It is certified that error appears in the above-identified patent and that said Letters Patent is hereby corrected as shown below:

<u>Title page,</u>
Item [73], Assignee, delete "Biotechnology Australia Pty Limited, New South Wales, Australia" and substitute therefor -- TECRA INTERNATIONAL PTY. LTD., Melbourne, Victoria, Australia --.

Signed and Sealed this

Thirteenth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,004,766
DATED        : December 21, 1999
INVENTOR(S)  : Vincent H. Atrache et al.

It is certified that error appears in the above-identified patent and that said Letters Patent is hereby corrected as shown below:

<u>Title page,</u>
Item [73], Assignee, delete "Melboume, Victoria, Australia" and substitute therefore -- Melbourne, Victoria, Australia --.

Signed and Sealed this

Twenty-sixth Day of July, 2005

JON W. DUDAS
*Director of the United States Patent and Trademark Office*